(12) United States Patent
De Vos

(10) Patent No.: US 8,434,477 B2
(45) Date of Patent: May 7, 2013

(54) CAPSULE, FILLED WITH A MEDICINE, IN PARTICULAR AN INHALABLE MEDICINE

(75) Inventor: Dick De Vos, Oegstgeest (NL)

(73) Assignee: Pharmachemie B.V., Haarlem (NL)

(*) Notice: Subject to any disclaimer, the term of this patent is extended or adjusted under 35 U.S.C. 154(b) by 969 days.

(21) Appl. No.: 12/518,773

(22) PCT Filed: Dec. 12, 2007

(86) PCT No.: PCT/NL2007/000314
§ 371 (c)(1),
(2), (4) Date: Jun. 11, 2009

(87) PCT Pub. No.: WO2008/072956
PCT Pub. Date: Jun. 19, 2008

(65) Prior Publication Data
US 2010/0132705 A1    Jun. 3, 2010

(30) Foreign Application Priority Data
Dec. 13, 2006  (NL) ..................................... 1033047

(51) Int. Cl.
*A61M 15/00*    (2006.01)
(52) U.S. Cl.
USPC ................................. 128/203.21; 128/203.15
(58) Field of Classification Search ............. 128/203.15, 128/203.21
See application file for complete search history.

(56) References Cited

U.S. PATENT DOCUMENTS

| 3,991,761 | A  | * | 11/1976 | Cocozza ................... 128/203.15 |
| 4,338,931 | A  | * | 7/1982 | Cavazza ................... 128/203.15 |
| 5,048,514 | A  | * | 9/1991 | Ramella ................... 128/203.21 |
| 6,488,027 | B1 |   | 12/2002 | Moulin |
| 6,705,313 | B2 | * | 3/2004 | Niccolai ................... 128/203.21 |
| 7,559,325 | B2 | * | 7/2009 | Dunkley et al. .......... 128/203.21 |
| 2004/0159322 | A1 | * | 8/2004 | Kladders et al. ......... 128/203.15 |
| 2008/0308103 | A1 | * | 12/2008 | Lancesseur et al. ...... 128/203.21 |

FOREIGN PATENT DOCUMENTS

| EP | 0 180 543 B1 | 5/1986 |
| FR | 2 235 848 | 1/1975 |
| GB | 1 442 121 | 7/1976 |
| GB | 1 485 163 | 9/1977 |
| WO | WO-02/083220 A2 | 10/2002 |

* cited by examiner

*Primary Examiner* — Lynne Anderson
(74) *Attorney, Agent, or Firm* — RatnerPrestia

(57) ABSTRACT

An assembly of a tube-shaped body and a tube-shaped cap, which are open at one distal side, is provided to manufacture a capsule for enclosing a medicine. At least one recess is arranged in an outer surface of the body, wherein at least one fixating bulge is arranged in an inner surface of the cap, which is destined to be snugly received in the recess in the outer surface of the body in order to realize a fixed snap connection between the body and the cap. A smallest inner diameter of the fixating bulge of the cap is equal to or smaller than a smallest outer diameter of the recess in the body, which contributes to realizing a fixed snap connection which is firm to such an extent that the capsule is suitable for application in an inhalation apparatus comprising provisions for piercing the capsule at least one place.

14 Claims, 2 Drawing Sheets

CAPSULE, FILLED WITH A MEDICINE, IN PARTICULAR AN INHALABLE MEDICINE

CROSS-REFERENCE TO RELATED APPLICATIONS

This application is the U.S. national phase application of PCT International Application No. PCT/NL2007/000314, filed Dec. 12, 2007, which claims priority to Netherlands Patent Application No. 1033047, filed Dec. 13, 2006, the contents of such applications being incorporated by reference herein.

FIELD OF THE INVENTION

The present invention relates to an assembly of a tube-shaped basic body and a tube-shaped cap, which are open at one distal side, and which are destined to be connected to each other by means of a snap connection and forming a capsule for enclosing a quantity of medicine in doing so, wherein fixating means comprising fixating parts which are adapted to engage each other tightly in order to realize a fixed snap connection are provided, wherein one of the fixating parts is arranged on one of an outer surface of the basic body and an inner surface of the cap, and wherein another of the fixating parts is arranged on another of the outer surface of the basic body and the inner surface of the cap.

BACKGROUND OF THE INVENTION

Such an assembly is known from GB 1 442 121. This publication shows a capsule in which the basic body can be slid into the cap along a certain distance in order to realize a releasable closure of the capsule, and wherein it is also possible to slide the cap further into the cap in order to realize a total closure. There is a need for a releasable closure in view of a situation prior to filling the capsule, in which it is common that the basic body and the cap are transported together and are offered to a machine for filling the capsule together. In the filling machine, the basic body and the cap are pulled apart, for example under the influence of a vacuum, after which the filling is supplied, and the basic body and the cap are joined again. In that situation, there is a need for realizing a total closure, wherein it is not possible to separate the basic body and the cap from each other under normal circumstances.

For the purpose of realizing the releasable closure, axial ridges are arranged on an inner surface of the cap, which are extending in a longitudinal direction, and which are adapted to contact an outer surface of the basic body, wherein the cap is retained under the influence of friction between the axial ridges of the cap and the outer surface of the basic body. The connection between the basic body and the cap on the basis of friction can be released by applying forces which are higher than the friction forces, for example vacuum forces.

For the purpose of realizing the total closure, circumferential ridges are arranged on the inner surface of the cap, which are extending over a portion of a circumference of the cap, wherein the basic body has a circumferential area which is adapted to slide over the circumferential ridges and subsequently retain the circumferential ridges. In particular, the circumferential area is realized on the basis of a constriction of the basic body. When the basic body and the cap are slid into each other, the basic body and the cap are being pressed apart somewhat, in a radial direction, until the circumferential ridges are entirely located in the circumferential area. At that moment, the basic body and the cap resume their original shapes, and a form closure is realized, which can not be released under normal circumstances, in particular the circumstances which will further be encountered by the capsule. In particular, the basic body and the cap can no longer be slid from each other, because an outer diameter of a portion of the basic body over which the circumferential ridges should be pulled in that case is larger than an inner diameter of the circumferential edges, at the position of an area of the circumferential ridges located most to an inside. On the basis of this fact, the obtained form closure can also be indicated as snap connection.

For sake of completeness, it is noted that in respect of both the axial ridges and the circumferential ridges, it is true that these are positioned over the circumference of the cap with a certain intermediate space, so that air can escape when the basic body and the cap are being slid into each other.

SUMMARY OF THE INVENTION

It is an object of the present invention to provide an assembly of a basic body and a cap as described above, with which it is possible to realize an extra solid and secure closure of the capsule which is manufactured on the basis of the basic body and the cap, after supply of the filling of the capsule has taken place. This object is achieved by providing an assembly as described in the first paragraph, wherein an inner diameter of the fixating part on the inner surface of the cap, at the position of a most far projecting area of this fixating part, is at the most equal to an outer diameter of the fixating part on the outer surface of the basic body, at the position of a most far projecting area of this fixating part.

Preferably, the fixating means comprise a combination of at least one bulge and at least one recess which is adapted to snugly receive the bulge. For sake of clarity, in the following explanation of the present invention, it will be assumed that the at least one bulge is arranged in the inner surface of the cap, and that the at least one recess is arranged in the outer surface of the basic body. That does not alter the fact that an opposite situation is also possible, i.e. a situation in which the at least one bulge is arranged in the outer surface of the basic body, and that the at least one recess is arranged in the inner surface of the cap.

When the present invention is applied, it is achieved that when the basic body and the cap are slid into each other so far that the fixating bulge of the cap is received in the recess in the basic body, a form closure is realized. In the case that the inner diameter of the fixating bulge of the inner surface of the cap, at the position of an area of the fixating bulge located most to an inside, is smaller than an outer diameter of the recess in the outer surface of the basic body, at the position of an area of the recess located most to an inside, a press fit is obtained, which offers extra firmness on the basis of a permanent deformation of the basic body and/or the cap. This is a consequence of the fact that prior to joining the basic body and the cap, a smallest inner diameter of the fixating bulge of the cap is smaller than a smallest outer diameter of the recess in the basic body. In that situation, the basic body and the cap are not only fixed with respect to each other on the basis of a snap connection, wherein the basic body and the cap deform temporarily until the fixating bulge of the cap is fully received in the recess of the basic body. Also, a permanent deformation of the basic body and/or the cap takes place, wherein the basic body and or the cap are inclined to move toward each other in a radial direction, so that extra forces need to be overcome when it would be intended to move the basic body and the cap apart.

An important advantage of the assembly of the basic body and the cap according to the present invention is that on the basis of this, it is possible to compose a capsule with a closure which is so strong that during further processing and handling of the capsule, there is practically no risk of the basic body and the cap getting disconnected. Therefore, it is not necessary to apply a seal, which is often done in certain applications in which the capsule is subjected to pulling forces in order to obtain an extra, exterior connection between the basic body, and the cap. Such a seal comprises a gelatine ribbon, for example, and is extending over adjoining outer surfaces of the basic body and the cap, wherein the seal is attached to both outer surfaces.

In a practical embodiment of the assembly according to the present invention, a number of fixating bulges is arranged in the inner surface of the cap, which are evenly distributed over a circumference of the cap, and which are located substantially at an equal longitudinal position on the cap. In this way, a good closure of the capsule is guaranteed, over the entire circumference thereof, while it is also possible to let air escape when the basic body and the cap are slid into each other for the purpose of closing the capsule as a consequence of the intermediate spaces between the fixating bulges.

Preferably, in the inner surface of the cap, at a position closer to the open distal side of the cap than the fixating bulge, at least one retaining bulge is arranged, which is destined to be releasably received in the recess in the outer surface of the basic body in order to realize a releasable snap connection, wherein an inner diameter of the retaining bulge, at the position of an area of this bulge located most to an inside, is larger than an inner diameter of the fixating bulge, at the position of an area of this bulge located most to an inside, and is larger than the outer diameter of the recess in the outer surface of the basic body, at the position of the area of the recess located most to an inside. On the basis of the presence of the retaining bulge, which is smaller than the fixating bulge, a temporary connection between the basic body and the cap can be realized prior to filling of the capsule, as is also the case with the assembly known from GB 1 442 121.

In a practical embodiment of the assembly according to the present invention, a number of retaining bulges is arranged in the inner surface of the cap, which are evenly distributed over a circumference of the cap, and are located substantially at an equal longitudinal position on the cap. In this way, a good releasable closure of the capsule over the entire circumference thereof is guaranteed, while it is also possible to let air escape when the basic body and the cap are slid into each other for the purpose of establishing the temporary closure, as a consequence of intermediate spaces between the retaining bulges.

It is also practical when a single recess is arranged in the outer surface of the basic body, which is extending over an entire circumference of the basic body. For example, such a recess can be realized in a relatively simple way by providing the basic body with a constriction, as is the case with the basic body known from GB 1 442 121.

Furthermore, the present invention relates to a capsule which is filled with a medicine, and which is manufactured on the basis of the above-described assembly according to the present invention, wherein the basic body and the cap are connected to each other by means of a fixed snap connection, and wherein the fixating bulge in the inner surface of the cap is received in the recess in the outer surface of the basic body. The medicine with which this capsule is filled can be any medicine that is suitable to be enclosed by a capsule, and can be an inhalable medicine, for example. Moreover, the medicine can have any suitable shape, and can be in the shape of powder, for example.

Preferably, both the basic body and the cap are manufactured from a material which is common in the context of capsules filled with a medicine, for example gelatin or hydroxy propyl methyl cellulose (HPMC).

Furthermore, the present invention relates to a capsule which is particularly destined to be applied in an inhalation apparatus, and which is filled with an inhalable medicine.

An inhalation apparatus is known per se, for example from GB 1 485 163, and comprises a space having two compartments, namely a compartment which is suitable for receiving a capsule which is filled with an inhalable medicine, and a larger compartment which is directly in communication with it. For sake of clarity, the first compartment will hereinafter be indicated as capsule receiving compartment, while the latter compartment will hereinafter be indicated as mixing chamber.

The inhalation apparatus comprises a number of movably arranged needles for piercing the capsule when this is located in the capsule receiving space, so that a number of holes can be made in the capsule, through which the content thereof can be released. Furthermore, the inhalation apparatus is provided with means for conducting air through the apparatus, in particular through the mixing chamber. The inhalation apparatus known from GB 1 485 163 comprises two channels for supplying air to the mixing chamber, wherein the channels are connected to the mixing chamber at different positions, and wherein longitudinal axes of the channels are extending in directions which are substantially corresponding to directions of tangents to the mixing chamber. Furthermore, the inhalation apparatus comprises a suction tube which is also connected to the mixing chamber.

The inhalation apparatus is applicable for administering an inhalable medicine, wherein a user of the inhalation apparatus takes in the medicine himself/herself. Roughly speaking, the functioning of the inhalation apparatus known from GB 1 485 163 is as follows. Firstly, the user places a capsule which is filled with an inhalable medicine in the capsule receiving space of the inhalation apparatus. In view of placing and removing of capsules, the inhalation apparatus is constructed in such a way that the capsule receiving space can be opened and closed. Subsequently, the user operates the needles for piercing the capsule, and after that, the user exerts a suction force, through the suction tube. As a consequence of the under pressure which is obtained owing to this, air is supplied to the mixing chamber by the two channels, and as a consequence of the positioning of the two channels, an air swirl is obtained in the process, in the mixing chamber. Under the influence of the suction force, the capsule is displaced from the capsule receiving space to the mixing chamber, and under the influence of the air swirl in the mixing chamber, the capsule starts to rotate, wherein the capsule regularly collides against walls of the mixing chamber. The rotation movement and the collisions of the capsule contribute to emptying of the capsule. Under the influence of the air flow which is realized in the suction tube by the user of the inhalation apparatus, the inhalable medicine is supplied to the mouth or nose of the user through the suction tube. Apart from that, at the position of a connection of the suction tube to the mixing chamber, a grate is arranged, so that it is prevented that the capsule exits the mixing chamber.

In respect of a capsule which is destined to be applied in an inhalation apparatus, it is important that the parts of which the capsule is composed are tightly connected to each other. It has appeared in practice that when the capsule is pierced by the needles and the needles are subsequently retracted, the capsule parts are inclined to move along with the needles and to move apart as a consequence thereof under the influence of adhesion forces between the needles and the walls of the openings just created. When this actually happens and the connection between the capsule parts is broken, the capsule parts are slid apart until they touch walls of the capsule receiving space, at both sides. The capsule which is extended in this way is then stuck in the capsule receiving space, as a result of which the inhalation apparatus is malfunctioning, because the capsule can no longer move freely in the mixing chamber. Moreover, in such a case, it is bothersome for the user to remove the capsule from the capsule receiving space.

According to the state of the art, for the purpose of the connection of the parts of a capsule, a seal is applied, which is arranged over outer surfaces of the parts. Also, solutions are provided which are having for an object decreasing the adhesion forces between the needles and the walls of the openings in the capsule. For example, it is described in U.S. Pat. No. 6,488,027 that it is advantageous when the needle is manufactured from metal and is provided with a layer of a copolymer, wherein Teflon is a practical possibility.

It is an object of the present invention to provide a capsule in which the connection between the parts of which the capsule is composed is sufficiently strong to enable application of the capsule in an inhalation apparatus, while the seal is omitted, without a risk that the connection between the parts is broken when the capsule is pierced and the needles or other means which are applied to this end are retracted. Omitting the seal has as an important advantage that the number of steps of the manufacturing and filling process of the capsule is reduced, as a result of which this process takes less time and, as a consequence, costs less money. The object is achieved by providing a capsule which is filled with an inhalable medicine, and which comprises parts which are connected to each other exclusively through a fixed snap connection.

In general, for the purpose of realizing a snap connection, use is made of a bulge and a recess for receiving the bulge, wherein the bulge is arranged in one part, and the recess in another part. When the material of the parts is somewhat flexible, the parts can be moved over each other, wherein the parts are pressed apart to some extent as long as the bulge is not yet fully located in the recess. However, as soon as the bulge reaches the correct position in the recess, the parts resume their original shape. In that situation, it is not just possible to move the parts still further with respect to each other, or to realize a reverse movement, because the bulge is retained by a barrier which is being formed by a portion of a wall of the recess.

In a practical embodiment, the capsule according to the present invention comprises the following parts:
- a tube-shaped basic body, wherein at least one recess is arranged in an outer surface of the basic body, and wherein the basic body is open at one distal side; and
- a tube-shaped cap, wherein at least one bulge is arranged in an inner surface of the cap, and wherein the cap is open at one distal end;

wherein the basic body and the cap are connected to each other exclusively by means of a fixed snap connection, wherein the bulge of the inner surface of the cap is snugly received in the outer surface of the basic body.

Furthermore, the present invention relates to a method for releasing an inhalable medicine. According to this method, a capsule is provided which is filled with an inhalable medicine, and which comprises parts which are connected to each other by means of a fixed snap connection, and at least one hole is arranged in the capsule. The method can furthermore comprise the step of moving the capsule.

Furthermore, the present invention relates to an assembly of an inhalation apparatus and a capsule which is filled with an inhalable medicine, and which comprises parts which are connected to each other by means of a fixed snap connection, wherein the inhalation apparatus comprises an interior space which, among other things, is suitable for receiving the capsule; and means which are adapted to make at least one hole in the capsule. Preferably, these latter means comprise at least one movably arranged needle.

The inhalation apparatus which is part of the assembly according to the present invention can for example be the inhalation apparatus known from GB 1 485 163. In particular, the inhalation apparatus can comprise at least two holes for passing on air to the interior space, wherein the air passage holes are located at different positions with respect to the space, so that in a situation in which air is supplied to the space through the holes, an air swirl in the space is obtained. In this way, with the help of the inhalation apparatus, a rotation of the capsule can be realized, which contributes to a good course of the process of emptying the capsule.

Furthermore, the present invention relates to a method for releasing an inhalable medicine, comprising the following steps:
- providing an assembly of an inhalation apparatus and a capsule according to the present invention, as described above;
- positioning the capsule in the interior space of the inhalation apparatus;
- activating the means of the inhalation apparatus which are adapted to make at least one hole in the capsule; and
- conducting air through the space of the inhalation apparatus.

Preferably, the method furthermore comprises the step of letting the capsule move in the interior space of the inhalation apparatus. This step can be realized by carrying out the step of conducting air through the internal space, for example, when an air swirl is realized in the process, in the interior space, as a result of which the capsule can be brought to rotation.

BRIEF DESCRIPTION OF THE DRAWINGS

The present invention will further be explained on the basis of the following description. With this, reference will be made to the drawing, in which equal reference signs indicate equal or similar components, and in which.

DETAILED DESCRIPTION OF THE INVENTION

Figure 1:
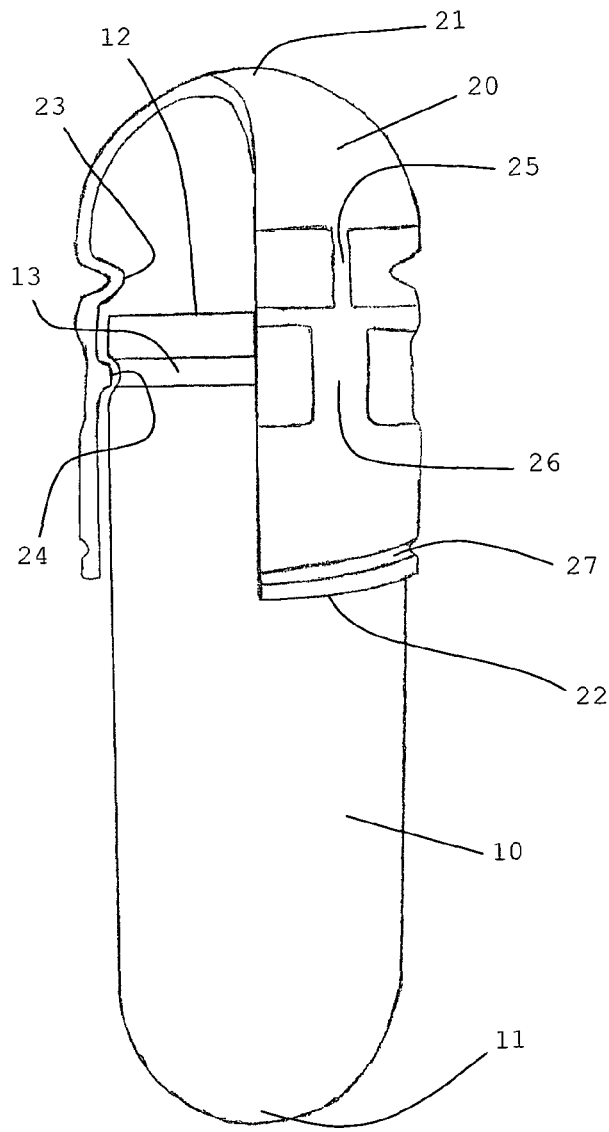
FIG. 1 diagrammatically shows a partially cut-away perspective view of an assembly of a basic body and a cap according to the present invention.
Figure 2:
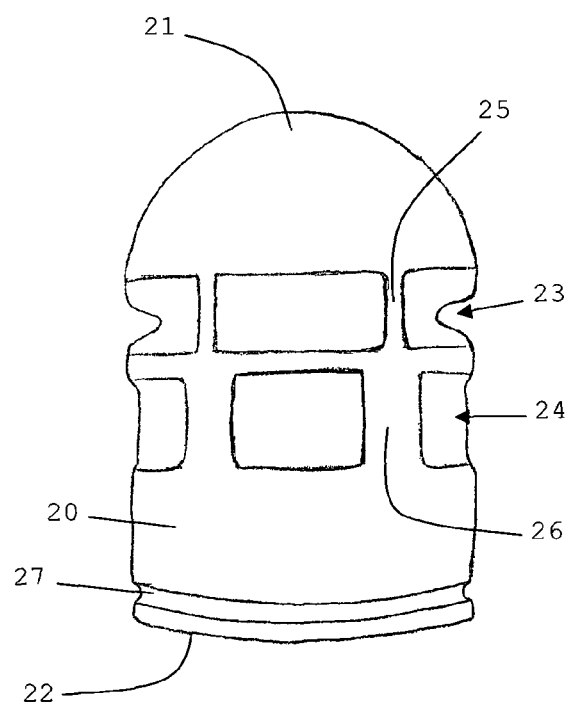
FIG. 2 diagrammatically shows a side view of the cap shown in FIG. 1.

FIG. 1 shows an assembly of a basic body 10 and a cap 20 according to the present invention, and FIG. 2 shows a side view of the cap 20.

Both the basic body 10 and the cap 20 are tube-shaped, wherein one side 11, 21 is closed, and wherein another side 12, 22 is open.

In the shown example, an outer diameter of the basic body 10 is equal for any longitudinal position, except at the position of a recess 13 which is located close to the open side 12 of the basic body 10, where the outer diameter is smaller.

The cap 20 comprises a number of bulges 23, 24 which are directed inwardly. In the following, bulges 23 which are located at a position closer to the closed side 21 of the cap 20 are indicated as fixating bulges 23, and bulges 24 which are located at a position closer to the open side 22 of the cap 20 are indicated as retaining bulges 24. In respect of both types of bulges 23, 24, it is true that they are evenly distributed over a circumference of the cap 20, wherein intermediate spaces 25, 26 are present between the bulges 23, 24. Close to the open side 22 of the cap 20, a groove 27 is arranged in an outer surface of the cap 20, over the entire circumference of the cap 20.

In the shown example, a smallest inner diameter of the fixating bulges 23 of the cap 20 is smaller than a smallest outer diameter of the recess 13 in the basic body 10. A smallest inner diameter of the retaining bulges 24 of the cap 20 is larger than the smallest inner diameter of the fixating bulges 23. The smallest inner diameter of the retaining bulges 24 of the cap 20 is also larger than a smallest outer diameter of the recess 13 in the basic body 10, and smaller than an outer diameter of the other portion of the basic body 10.

FIG. 1 shows a mutual position of the basic body 10 and the cap 20 in which the cap 20 is partially slid over the basic body 10, and wherein the retaining bulges 24 of the cap 20 are located at the position of the recess 13 in the basic body 10. In this mutual position, on the basis of the fact that the retaining bulges 24 of the cap 20 are located in the recess 13 of the basic body 10, a snap connection between the basic body 10 and the cap 20 is realized. A difference of inner diameter between the retaining bulges 24 of the cap 20 and an adjacent area located closer to the open side 22 of the cap 20 is relatively small, so that only a relatively small barrier needs to be bridged when it is intended to break the snap connection between the basic body 10 and the cap 20. On this basis, the snap connection which is established on the basis of a cooperation between the recess 13 in the basic body 10 and the retaining bulges 24 of the cap 20 is typified as releasable snap connection.

Figure 3:
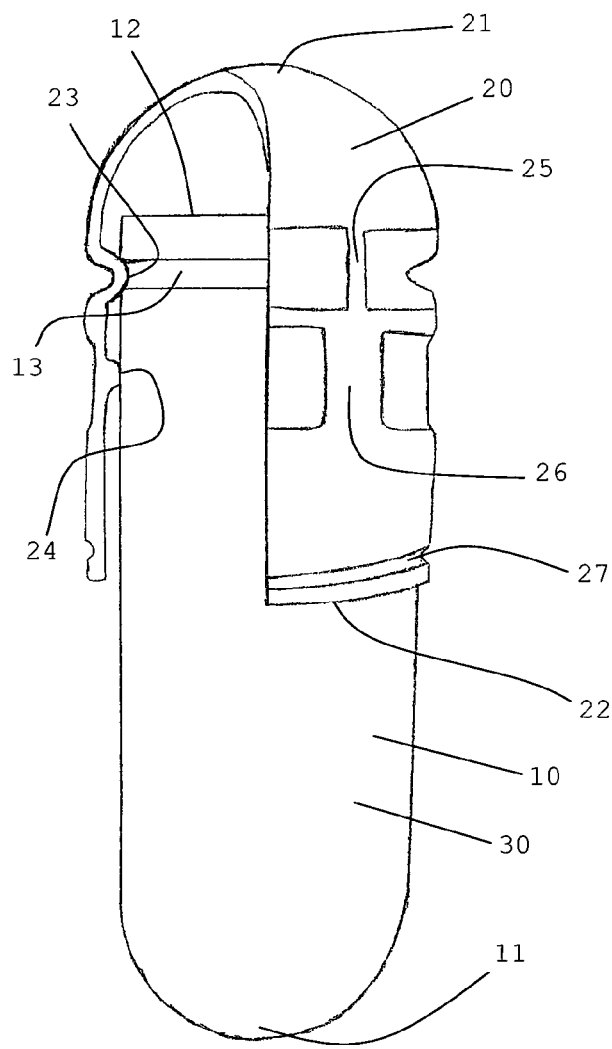
FIG. 3 diagrammatically shows a partially cut-away perspective view of a capsule according to the present invention, which comprises the basic body shown in FIG. 1 and the cap shown in FIG. 1.

The mutual position of the basic body 10 and the cap 20 as shown in FIG. 1, wherein the cap 20 is partially slid over the basic body 10, and wherein the retaining bulges 24 of the cap 20 are located at the position of the recess 13 in the basic body 10 is a position in which the assembly of basic body 10 and cap 20 is transported and is supplied to a machine (not shown) for detaching the basic body 10 and the cap 20, filling the basic body 10 with a filling agent, for example a medicine, and putting the cap 20 back on the basic body 10, wherein a fixed snap connection is realized in order to obtain a tightly closed capsule 30. This capsule 30 is shown in FIG. 3. The way in which the capsule 30 is manufactured on the basis of the assembly of the basic body 10 and the cap 20 as shown in FIG. 1 will hereinafter be further explained.

In a first step, the snap connection between the basic body 10 and the cap 20 is broken by moving the basic body 10 and the cap 20 apart under the influence of suitable pulling forces, for example vacuum forces. When the cap 20 has been removed from the basic body 10, an interior space of the basic body 10 is freely accessible through the open side 12, and the basic body 10 can be filled. The filling agent can be a medicine, for example, and can have any suitable shape. For example, the basic body 10 can be filled with a powder or small tablets.

After the step of filling the basic body 10 has taken place, the cap 20 is slid over the basic body 10 again. The basic body 10 and the cap 20 are moved toward each other, until the fixating bulges 23 of the cap 20 are located at the position of the recess 13 in the basic body 10. During the relative movement of the basic body 10 and the cap 20, air can escape through the intermediate spaces 25, 26 of the bulges 23, 24 of the cap 20.

As a consequence of the fact that the smallest inner diameter of the fixating bulges 23 of the cap 20 is smaller than the smallest outer diameter of the recess 13 in the basic body 10, exertion of pressure is necessary to eventually take care that the fixating bulges 23 of the cap 20 end up at the position of the recess 13 in the basic body 10. In the process, a permanent deformation of the basic body 10 and/or the cap 20 is obtained, and a press fit is thus obtained. Once the fixating bulges 23 of the cap 20 are at the position of the recess 13 in the basic body 10, a fixed snap connection is realized, which is practically not releasable without damaging the capsule 30 obtained in this way.

The groove 27 in the outer surface of the cap 20 does not have a function in establishing a snap connection between the basic body 10 and the cap 20. For sake of completeness, it is noted that this groove 27 plays a role in guaranteeing a desired circular shape of a cross-section of the cap 20 during a manufacturing process of the cap 20, in particular during a step in which the material of the cap 20 is dried. Due to the presence of the groove 27, it is prevented that the cross-section of the cap 20 gets an oval shape. As a matter of fact, the application of the groove 27 is known per se from EP 0 246 804.

The basic body 10 and the cap 20 can be made of any suitable material. Examples of common materials for capsules 30 are gelatin and HPMC.

On the basis of the fact that the parts 10, 20 of the capsule 30 are connected to each other very tightly on the basis of a fixed snap connection, wherein the cap 20 is clamped tightly on the basic body 10, it is not necessary to arrange extra connection means such as a sealing ribbon on the capsule 30. Due to this, a step in the manufacturing process of the capsule 30 is saved, which contributes to a reduction of the cost prize of the capsule 30.

Figure 4:
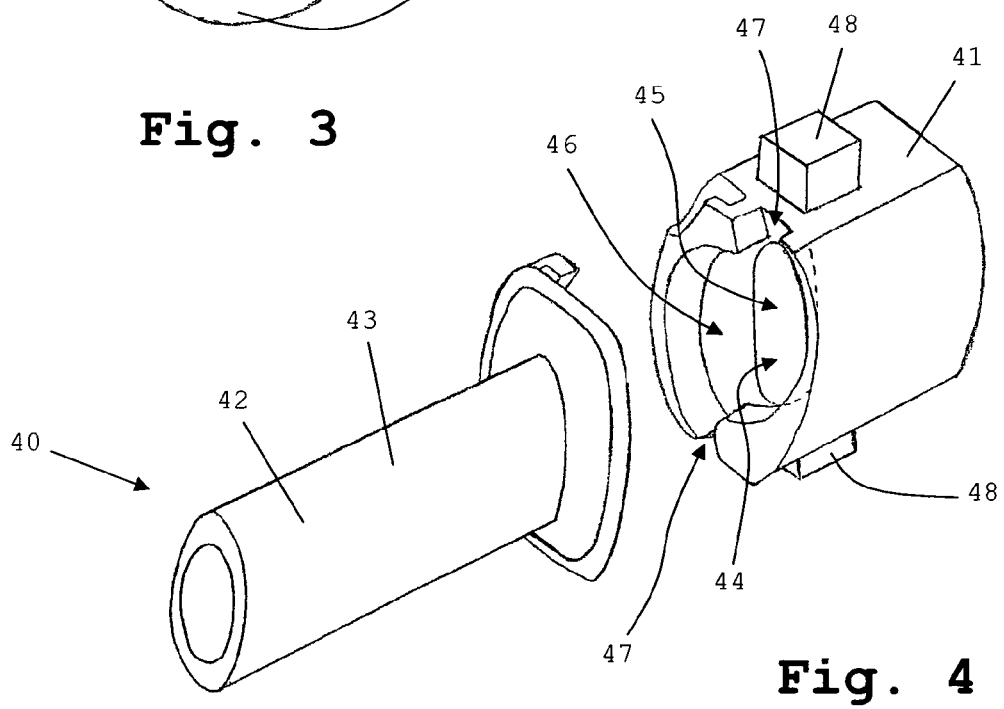
FIG. 4 diagrammatically shows an exploded drawing of an inhalation apparatus.

The capsule 30 according to the present invention is suitable for a variety of applications. An application which will be described below is the application in an inhalation apparatus 40 as shown in FIG. 4.

The inhalation apparatus 40 comprises an inhalation housing 41 and a mouthpiece 42 having a suction tube 43. In an assembled condition of the inhalation apparatus 40, the inhalation housing 41 and the mouthpiece 42 are connected to each other, wherein it is possible to rotate the inhalation housing 41 and the mouthpiece 42 with respect to each other about a rotation axis extending in a longitudinal direction.

The inhalation housing 41 comprises an interior space 44, wherein a compartment 45 of this interior space 44 is suitable for receiving a capsule 30. This compartment 45 will hereinafter be indicated as capsule receiving space 45, while another part of the interior space 44 of the inhalation housing 41 will hereinafter be indicated as mixing chamber 46. For the purpose of air supply to the mixing chamber 46, two cavities 47 are arranged in the inhalation housing 41.

In the inhalation housing 41, two groups of four needles (not shown) are disposed, at such positions that they are capable of piercing a capsule 30 which is located in the capsule receiving space 45, at both distal ends. The groups of needles are operable by means of push-buttons 48.

The inhalation apparatus 40 is applied by a user to take in the content of a capsule 30 with an inhalable medicine. To this end, the user first puts the inhalation housing 41 and the mouthpiece 42 in a mutual position in which the interior space 44 of the inhalation housing 41 is freely accessible, places a capsule 30 in the capsule receiving space 45 of the inhalation housing 41, and subsequently puts the inhalation housing 41 and the mouthpiece 42 in a position in which the mouthpiece 42 is located in a straight line in front of the capsule 30. In this mutual position of the inhalation housing 41 and the mouthpiece 42, the interior space 44 of the inhalation housing 41 is in communication with the outside air only through the cavities 47 and the suction tube 43 of the mouthpiece 42.

After the capsule 30 has been placed in the inhalation apparatus 40, the user operates the push-buttons 48, so that the needles penetrate the capsule 30 and make holes in the capsule 30. Subsequently, the user creates an underpressure in the interior space 44 of the inhalation housing 41 by exerting a suction force with mouth or nose, through the suction tube 43 of the mouthpiece 42. As a consequence of this under pressure, air is sucked in, through the cavities 47. The shape of the mixing chamber 46 and the positioning of the cavities 47 are such that an air swirl is created in the mixing chamber 46. As a consequence of the suction force which is exerted by the user, the capsule 30 is sucked from the capsule receiving space 45 into the mixing chamber 46. In the mixing chamber 46, the capsule 30 is taken along by the air swirl, and starts carrying out a rotation movement due to this. As a consequence of this movement, and the fact that the capsule 30 regularly collides with walls of the mixing chamber 46, the capsule 30 is emptied through the holes arranged in it, after which the released medicine is displaced through the suction tube 43 of the mouthpiece 42, in the direction of mouth or nose of the user of the inhalation apparatus 40. Apart from that, a grate (not shown) is arranged at an entrance of the suction tube 43 of the mouthpiece 42, so that it is prevented that the capsule 30 can leave the mixing chamber 46 and end up in the suction tube 43.

In the use of the inhalation apparatus 40, it is important that a capsule 30 having a firm connection between the basic body 10 and the cap 20 is applied. Due to this, it is prevented that the basic body 10 and the cap 20 are pulled apart when the needles retract after piercing the closed sides 11, 21 of the basic body 10 and the cap 20, which happens as soon as the user releases the push-buttons 48, and a good and reliable functioning of the inhalation apparatus 40 is guaranteed.

It will be clear to a person skilled in the art that the scope of the present invention is not limited to the examples discussed in the foregoing, but that several amendments and modifications thereof are possible without deviating from the scope of the invention as defined in the attached claims.

In the foregoing, among other things, an assembly of a tube-shaped basic body 10 and a tube-shaped cap 20 is described, wherein both the basic body 10 and the cap 20 are open at one distal side 12, 22. The assembly is provided to manufacture a capsule 30 for enclosing a medicine.

At least one recess 13 is arranged in an outer surface of the basic body 10, wherein at least one fixating bulge 23 is arranged in an inner surface of-the cap 20, which is destined to be snugly received in the recess 13 in the outer surface of the basic body 10 in order to realize a fixed snap connection between the basic body 10 and the cap 20. A smallest inner diameter of the fixating bulge 23 of the cap 20 is equal to or smaller than a smallest outer diameter of the recess 13 in the basic body 10, which contributes to realizing a fixed snap connection which is firm to such an extent that the capsule 30 is suitable for application in an inhalation apparatus 40 comprising means for piercing the capsule 30 at at least one place.

The invention claimed is:

1. Assembly of a tube-shaped basic body and a tube-shaped cap, which are open at one distal side, and which are configured to be connected to each other by means of a snap connection and forming a capsule for enclosing a quantity of medicine in doing so, wherein fixating means comprising fixating parts which are adapted to engage each other tightly in order to realize a fixed snap connection are provided, wherein one of the fixating parts is arranged on one of the outer surface of the basic body and an inner surface of the cap, wherein at least one recess is arranged in an outer surface of the basic body, wherein at least one fixating bulge is arranged in an inner surface of the cap, which is configured to be snugly received in the recess in the outer surface of the basic body in order to realize a fixed snap connection, and wherein an inner diameter of the fixating bulge of the inner surface of the cap, at the position of an area of the fixating bulge located most to an inside is at the most equal to an outer diameter of the recess in the outer surface of the basic body, at the position of an area of the recess located most to an inside, wherein at least one retaining bulge is arranged in the inner surface of the cap, at a position closer to the open distal side of the cap than the fixating bulge, which is configured to be releasably received in the recess in the outer surface of the basic body in order to realize a releasable snap connection, wherein an inner diameter of the retaining bulge, at the position of an area of this bulge located most to an inside, is larger than an inner diameter of the fixating bulge, at a position of an area of this bulge located most to an inside, and is larger than the outer diameter of the recess in the outer surface of the basic body, at a position of the area of the recess located most to an inside.

2. Assembly according to claim 1, wherein a number of fixating bulges is arranged in the inner surface of the cap, which are evenly distributed over a circumference of the cap, and which are located substantially at an equal longitudinal position on the cap.

3. Assembly according to claim 1, wherein a number of retaining bulges is arranged in the inner surface of the cap, which are evenly distributed over a circumference of the cap, and which are located substantially at an equal longitudinal position on the cap.

4. Assembly according to claim 1, wherein a single recess is arranged in the outer surface of the basic body, which is extending over an entire circumference of the basic body.

5. Capsule which is filled with a medicine, and which is manufactured on the basis of an assembly according to claim 1, wherein the basic body and the cap are connected to each other by means of a fixed snap connection, and wherein the fixating bulge in the inner surface of the cap is received in the recess in the outer surface of the basic body.

6. Capsule according to claim 5, which is filled with an inhalable medicine.

7. Method for releasing an inhalable medicine, comprising the following steps:
providing a capsule according to claim 6; and
creating at least one hole in the capsule.

8. Method according to claim 7, further comprising the step of moving the capsule.

9. Assembly of an inhalation apparatus and a capsule according to claim 1, wherein the inhalation apparatus comprises an interior space which is suitable for receiving the capsule; and means which are adapted to make at least one hole in the capsule.

10. Assembly according to claim 9, wherein the means of the inhalation apparatus which are adapted to make at least one hole in the capsule comprise at least one movably arranged needle.

11. Assembly according to claim 9, wherein the inhalation apparatus comprises at least two holes for passing air to the interior space, wherein the air passage holes are located at different positions with respect to the space, so that in a situation in which air is supplied to the space through the holes, an air swirl in the space is obtained.

12. Method for releasing an inhalable medicine, comprising the following steps:
- providing an assembly of an inhalation apparatus and a capsule according to claim 9;
- positioning the capsule in the interior space of the inhalation apparatus;
- activating the means of the inhalation apparatus which are adapted to make at least one hole in the capsule; and
- conducting air through the interior space of the inhalation apparatus.

13. Method according to claim 12, further comprising the step of letting the capsule move in the interior space of the inhalation apparatus.

14. Method according to claim 13, wherein the step of letting the capsule move in the interior space of the inhalation apparatus is realized by carrying out the step of conducting air through the interior space of the inhalation apparatus.

* * * * *